United States Patent [19]

Cuatrecasas et al.

[11] 3,947,352

[45] Mar. 30, 1976

[54] POLYSACCHARIDE MATRICES FOR USE AS ADSORBENTS IN AFFINITY CHROMATOGRAPHY TECHNIQUES

[76] Inventors: Pedro Cuatrecasas, 10 Hillside Road; Indu Parikh, 4404 Keswick Road, both of Baltimore, Md. 21210

[22] Filed: May 31, 1974

[21] Appl. No.: 475,305

[52] U.S. Cl................. 210/31 C; 195/63; 195/68; 195/DIG. 11; 210/502; 260/9; 260/112 R; 260/121; 260/122; 260/212; 260/209 R; 260/209 D; 260/233.3 R; 260/234 D
[51] Int. Cl.[2].. B01D 15/08; C07G 7/00; C07H 1/00
[58] Field of Search........... 210/31 C; 260/9, 112 R, 260/121, 122, 212, 209 R, 209 D, 233.3 R, 234 D; 195/63, 68, DIG. 11

[56] References Cited
UNITED STATES PATENTS
3,850,798  11/1974  Sjöquist ........................ 210/31

OTHER PUBLICATIONS

Abstracts of Papers, Amer. Chem. Soc., 166th National Meeting, (Chicago, Ill. 1973), "Affinity Chromatography," Parikh et al.

*Primary Examiner*—Donald E. Czaja
*Assistant Examiner*—Edward Woodberry
*Attorney, Agent, or Firm*—William H. Benz; Norman H. Stepno

[57] ABSTRACT

Polysaccharide matrices, e.g., agarose, for use in certain affinity chromatography procedures, are activated with sodium metaperiodate, derivatized with a symmetrical dihydrazide and thence reductively stabilized, preferably with sodium cyanoborohydride. Moreover, intermediate Schiff bases formed from the $NaIO_4$-oxidized polysaccharide are selectively, reductively stabilized with said sodium cyanoborohydride.

19 Claims, 6 Drawing Figures

L = COUPLED AMINO LIGAND

A-CHO + NH$_2$-NH-CO-CH$_2$-CH$_2$-CO-NH-NH$_2$ ⟶ A=N-NH-CO-CH$_2$-CH$_2$-CO-NH-NH$_2$
(OXIDIZED AGAROSE)  (SUCCINIC DIHYDRAZIDE)

A=N-NH-CO-CH$_2$-CH$_2$-CO-NH-NH$_2$ + NaBH$_4$ ⟶ A-NH-NH-CO-CH$_2$-CH$_2$-CO-NH-NH$_2$
(HYDRAZIDO AGAROSE)

A-CNBr-ACTIVATED + NH$_2$-NH-CO-CH$_2$-CH$_2$-CO-NH-NH$_2$ ⟶ A-NH-NH-CO-CH$_2$-CH$_2$-CO-NH-NH$_2$

A-NH-NH-CO-CH$_2$-CH$_2$-CO-NH-NH$_2$ + HNO$_2$ ⟶ A-NH-NH-CO-CH$_2$-CH$_2$-CO-N$_3$
(NITROUS ACID)

A-NH-NH-CO-CH$_2$-CH$_2$-CO-N$_3$ + R-NH$_2$ ⟶ A-NH-NH-CO-CH$_2$-CH$_2$-CO-NH-R

A-NH-NH-CO-CH$_2$-CH$_2$-CO-NH-NH$_2$ + R-COOH ⟶ A-NH-NH-CO-CH$_2$-CH$_2$-CO-NH-NH-CO-R

*FIG. 3*

POLYSACCHARIDE MATRICES FOR USE AS ADSORBENTS IN AFFINITY CHROMATOGRAPHY TECHNIQUES

BACKGROUND OF THE INVENTION

1. Field of the Invention

The present invention relates to the activation of certain polysaccharide matrices for use in affinity chromatography procedures, and, more especially, to the sodium metaperiodate [$NaIO_4$] activation of polysaccharide matrices, to certain polyhydrazide derivatives thereof, to the "reductive stabilization" thereof and of such polyhydrazide derivatives, and to the coupling of various biologically active molecules thereto as well as to such polyhydrazide derivatives.

2. Description of the Prior Art

Affinity chromatography has found wide application in the purification of various biologically active molecules, such as small ligands, proteins, nucleotides and nucleosides. For example, nucleotides are cofactors and coenzymes in many biological systems and, therefore, many methods for attaching these compounds to insoluble matrices have been developed and applied. It is also known that certain polysaccharide matrices comprise the most useful solid supports in affinity chromatography. And various alternative methods exist to activate a polysaccharide matrix, e.g., cellulose, starch and cross-linked polysaccharide gels such as agarose, Sephadex and Sepharose, for the covalent attachment of, e.g., small ligands and proteins. Probably the most widely used technique at the present time for the covalent coupling of protein to insoluble matrices, finding considerable application in immunology and enzymology, is the cyanogen bromide method described in Axen et al, *Nature*, 214, 1302–1304 (1967); see also Cuatrecasas et al, *Proc. Natl. Acad. Sci. U.S.*, 61, 636–643 (1968). Briefly, cyanogen halides react rapidly with the hydroxyl groups of carbohydrates to form cyanate esters. The reaction occurs most rapidly at a pH between 10 and 12. The cyanate may react further with hydroxyl groups to form an imidocarbonate intermediate. It has been postulated from studies of low molecular weight model compounds, that the cyclic imidocarbonate is formed as a major product following the reaction of cyanogen halides with polymeric carbohydrates [FIG. 1A]. The highly reactive intermediate can be isolated, and agarose beads which contain this reactive group are commerically available [Pharmacia]. Imidocarbonates react with amines to form N-imidocarbonates [FIG. 1B] soureas [FIG. 1C] or N-carbamates [FIG. 1D]. However, the actual products formed in the reaction between cyanogen halide-activated agarose and the amino group of alanine, for example, are difficult to study owing to the insolubility of the carbohydrate and the relatively low concentrations of the products. Recent studies on the isoelectric point of products of the reaction between CNBr-activated polysaccharides and a primary amine indicate that an isourea is the major product, Svensson, *FEBS Lett.*, 29, 167 (1973). The technique of Axen et al, supra, characterizes the "titration method" of activation.

Despite the relative simplicity of the titration method of activation of agarose beads, a faster and safer alternative method has been developed. Cuatrecasas et al, *Anal. Biochem.*, in press. In this modification, the reaction is performed in carbonate buffer. The coupling efficiencies obtained are comparable to those observed after activation by the aforementioned titration method.

Generally considering the use of CNBr-activated gels, the amount of ligand coupled to the gel depends on the amount of CNBr added. Typically, this varies between 50 and 300 mg of CNBr per milliliter of packed beads. For example, with 200 mg of CNBr per milliliter of agarose and 0.5% albumin and 0.2 M $NaHCO_3$ at pH 9.5, approximately 5 mg of protein is bound per milliliter of packed gel. Similarly, if the concentration of low molecular weight ligand, e.g., alanine, is 0.1 M, the amount coupled is about 10 $\mu$ moles per milliliter of gel. The actual coupling efficiency will depend on the specific ligand used.

The quantity of CNBr and the exact composition of the buffer used in the coupling reaction should be adapted to the specific system under study. These conditions too have been described in detail, Cuatrecasas, *J. Biol. Chem.*, 245, 3059 (1970). A standard condition is the use of 200 mg of CNBr per milliliter of agarose, and of 0.2 M sodium bicarbonate at pH 9.5 as the buffer for the coupling reaction. Smaller quantities of CNBr, lower pH values, and high concentrations of ligand will decrease the probability of multipoint attachments of proteins [especially those of high molecular weight] to the gel, a condition that may lead to decreased or altered biological activity. In coupling macromolecules, e.g., concanavalin A or enzymes, it may be desirable to add ligands, e.g., competitive inhibitors, which bind to the active site of the protein. This may protect and perhaps prevent coupling through essential residues of the active site, and in addition, may stabilize the conformation of the protein so that the coupled protein will be more likely to retain its native structure.

In many cases, the interposition of spacers or "arms" between the matrix and the ligand greatly increases the effectiveness of the adsorbent. A variety of spacer molecules can be attached to agarose, and many chemical reactions exist that can be used to couple ligands and proteins to these derivatized agarose gels, Cuatrecasas, *J. Biol. Chem.*, supra. Diaminodipropylamine [Eastman] has been one of the most useful spacer molecules because it is relatively long and because it exhibits very minimal hydrophobic properties as compared to strictly methylenic diamine compounds such as hexamethylenediamine. Consider also copending application, Ser. No. 475,314 of the present inventors, filed concurrently herewith, and hereby expressly incorporated by reference. Whenever possible, it is advantageous to first attach such spacers to the ligand rather than to the gel since the adsorbents prepared in this way are less likely to exhibit nonspecific or ionic properties that can interfere in subsequent affinity chromatography experiments.

Nevertheless, CNBr is a toxic chemical, and awareness of the hazards associated with CNBr activation reactions is important. CNBr, which sublimes rather rapidly at room temperature, is a powerful lachrimator, and is highly toxic. Allowing the chemical to stand for months at room temperature can result in the formation of explosive compounds. Filtrates collected after activation contain large amounts of cyanide ion and should never be allowed to come to neutral or acidic pH. Disposal of the filtrates should be performed with care and only after the gaseous products are disssipated from the filter flask in a fume hood for several hours.

The importance of adequate ventilation during the activation procedures has been emphasized. Another disadvantage of the CNBr method for coupling amino group-containing ligands to agarose lies in the relative instability of the bond(s) formed between the ligand and the matrix. As a result, in most cases, during washing, storage and usage, a small amount of ligand is leaked out. This problem of ligand leakage is of great importance, especially during isolation of small [microgram] quantities of certain hormone receptors. The leakage of a ligand from the adsorbent becomes still more serious because the ligand which is released from the adsorbent in most cases has greater affinity toward the receptor protein(s) than the matrix-bound ligand. Besides the problem of ligand leakage, substitution does not work well with cellulose.

While nearly all of the earlier methods for coupling ligands or proteins to agarose depend on the initial modification of the gel with CNBr, an alternative method exists which is rapid, simple, and safe and which promises to result in chemically stable ligand-agarose bonds. This method depends on the oxidation of cis-vicinal hydroxyl groups of agarose [or cellulose] by sodium metaperiodate [NaIO$_4$] to generate aldehyde functions. Compare Sanderson et al, *Immunology*, 20, 1061–1065 (1971); see FIG. 2. These aldehydic functions react at pH 4–6 with primary amines to form Schiff bases [aldimines]; these are reduced with sodium borohydride [NaBH$_4$] to form stable secondary amines.

SUMMARY OF THE INVENTION

It has now been determined according to the invention that the "reductive stabilization" of the intermediate Schiff base is best achieved with sodium cyanoborohydride [NaBH$_3$CN] since this reagent, at a pH between 6 and 6.5, preferentially reduces Schiff bases without reducing the aldehyde functions of the agarose. Since sodium cyanoborohydride selectively reduces only the Schiff bases, it shifts the equilibrium of the reaction [FIG. 2] to the right and thereby drives the overall reaction to completion.

Moreover, very useful derivatives can be prepared according to the invention by allowing the periodate-oxidized agarose to react with a bifunctional, symmetrical dihydrazide [FIG. 3] most advantageously succinic dihydrazide. This reaction is quite advantageous since carbonyl groups react with hydrazides more completely than with primary amines. The matrix is thus converted to a hydrazido/hydrazone form and can be reduced with NaBH$_4$ or, preferably, NaBH$_3$CN, to produce unsymmetric hydrazides while the unreacted hydrazido groups are unaffected. The stable hydrazido-agarose derivatives can be stored and used at will for coupling proteins or ligands that contain carboxyl or amino groups with carbodiimide reagents according to known procedures or by conversion of the acyl hydrazide to the acyl azide form, also according to known procedures [FIG. 3]. A somewhat similar polyhydrazide-agarose has been prepared by coupling adipic dihydrazide to CNBr-activated agarose; Lamed et al, *Biochimica et Biophysica Acta*, 304, 231–235 (1973).

The polyhydrazide-matrix is also coupled to aldehyde or keto group containing ligands followed again by "reductive stabilization". Thus, the glycolipid, gangiloside, and certain glycoproteins are coupled to polyhydrazide-agarose [and cellulose] after periodate oxidation of suitable sugar component on the ligands.

Accordingly, polyhydrazide-agarose and -cellulose have been prepared utilizing the invention by reacting succinic dihydrazide with NaIO$_4$ oxidized matrix followed by reduction with NaBH$_4$ or NaBH$_3$CN. These polyhydrazides were easily converted to the corresponding acyl azides and coupled to proteins or peptides in mild fashion. By controlling the pH of the coupling reaction, the protein or peptide can be directed to couple solely through its $\alpha$-NH$_2$ group. And, again, the polyhydrazide matrix was also used to couple glycopeptides, glycoproteins, glycolipids and certain oligosaccharides after prior oxidation of the ligand with NaIO$_4$. Use of NaBH$_3$CN economized the quantitiy of ligand. Further, both brain gangliosides and thyroglobin were successfully coupled.

Although the periodate oxidation activation method for agarose generally results in a lower degree of liguid sustitution than can be achieved with the CNBr methods, the facility and safety of the method, and greater stability of the ligand-agarose bonds formed, offer considerable advantages. In many cases, enzyme purification by affinity chromatography is achieved satisfactorily with ligand substitution of 0.05–1.0 $\mu$ mole per milliliter of agarose, which can be readily achieved utilizing the procedures of the invention.

Other solid supports, such as cross-linked dextrans and cellulose, unlike agarose contain very large numbers of cis-vicinal hydroxyl groups and are thus very well suited for activation and coupling by the periodate oxidation procedures. Cellulose, because of its stability to the conditions of oxidation, can be substituted to a very high degree with the periodate method [see Table I]. The more porous Sephadex gels [G-75 and G-200] shatter after periodate treatment (5mM, 2 hours) and therefore are not recommended.

Table I

Incorporation of Radioactive Ligands Into Gels Activated By The Periodate/Hydrazide Procedures *

| Matrix | Incorporation | | |
|---|---|---|---|
| | SDH ($\mu$moles/ml) | Alanine ($\mu$moles/ml) | Albumin (mg/ml) |
| Agarose | 1.2 | 0.25 | 0.20 |
| Particulate cellulose | 210 | 1.1 | 0.21 |
| Beaded, porous cellulose | 500 | 1.1 | 0.16 |

* Gels were oxidized with 0.5 M sodium metaperiodate for 2 hours and allowed to react with excess succinic dihydrazide (SDH) as described in the text. SDH incorporation was calculated from elemental analysis.

DETAILED DESCRIPTION OF THE INVENTION

Figure 1A:
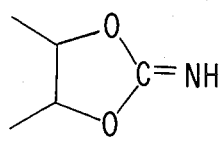
Figure 1B:
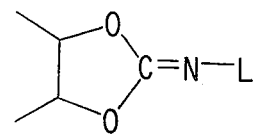
Figure 1C:
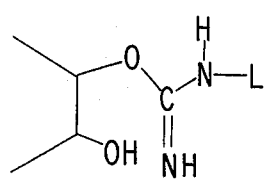
Figure 1D:
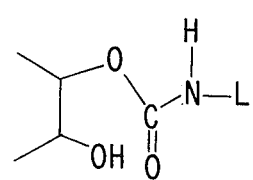
Figure 2:
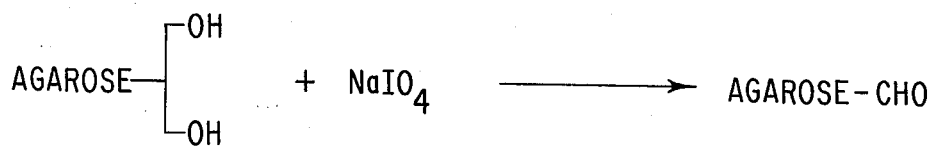
Figure 2:
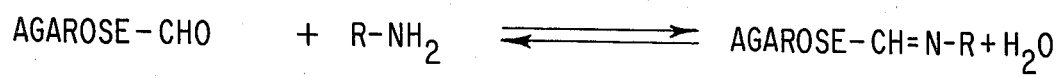
Figure 2:
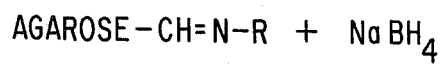
Figure 2:
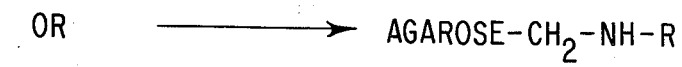
Figure 2:
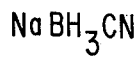

In order to further illustrate the present invention and the advantages thereof, the following specific examples are given, it being understood that same are intended only as illustrative and in no wise limitative.

Procedures for Sodium Periodate Oxidation of Agarose

To a suspension of 100 ml of agarose in 80 ml of water was added 20 ml of 1 M NaIO$_4$. The suspension, placed in a 500 ml tightly closed polyethylene bottle, was gently shaken on a mechanical shaker for 2 hours at room temperature. The oxidized agarose was filtered and washed on a coarse sintered-glass funnel with 2 liters of water.

Reductive Amination of Oxidized Agarose

Use of Sodium Borohydride

The washed, oxidized agarose was allowed to react with a solution of ligand containing an amino group. For example, an ω-aminoalkyl agarose derivative was prepared by adding the oxidized gel, 100 ml, to 100 ml of 2 M aqueous diaminodipropylamine [Eastman Chemicals] at pH 5.0. After 6-10 hours of gentle shaking at room temperature; the pH was raised to 9 with solid $Na_2CO_3$. Ten ml of freshly prepared 5 M $NaBH_4$ were added in small aliquots to the magnetically stirred suspension and kept at 4° over a 12-hour period with precautions to avoid excessive foaming. The reduced agarose derivative was washed in a 250 ml sintered-glass funnel with 2 liters of 1M NaCl without suction over a 4-hour period. After stopping the outflow [with a rubber stopper], the agarose derivative was incubated in an equal volume of 1 M NaCl for 15 hours while on the funnel, and washed with an additional 2 liters of 1 M NaCl over a 2-hour period. The filtrates of the wash were occasionally checked for the presence of free diamine by the TNBS* test or with ninhydrin. The extent of substitution of diamine, as determined by reaction with $^{14}C$-labeled acetic anhydride, was 2—3 μmoles per milliliter of agarose.

* 2,4,6-Trinitrobenzene sulfonic acid (TNBS); 2-3 drops of 1.5% ethanolic solution of TNBS are added to a mixture of 0.5 ml of filtrate and 0.5 ml of saturated sodium borate. The presence of diamine is indicated by formation of intense yellow color (420 nm) and of hydrazide by brick red color (500 nm).

Use of Sodium Cyanoborohydride

The product of reaction of the $NaIO_4$-oxidized agarose with the amino ligand was also subjected to reductive amination with sodium cyanoborohydride [$NaBH_3CN$]. Although sodium borohydride is efficient, the use of $NaBH_3CN$ can be most advantageous, e.g., when the quantity of the amino ligand is limited. Since the latter reducing agent drives the reaction toward completion, relatively more efficient use of the amino ligand results. This method is also preferably when the ligand to be coupled is sensitive to the higher pH values [pH 9-10] necessary with $NaBH_4$.

A between 1 to 50 mM solution of the amino ligand, a designation which includes proteins as well as smaller molecules, in 0.5 M phosphate buffer at pH 6, containing 0.5 mM sodium cyanoborohydride [Alfa Chemicals] was prepared at room temperature and centrifuged at 3000 g for 10 minutes to remove insoluble material. The pH of the solution was adjusted to 6. The solution was then added to an equal volume of periodate-oxidized agarose which had previously been washed with 1-2 volumes of 0.5 M phosphate buffer at pH 6. The suspension was gently shaken for 3 days in a closed, capped polyethylene bottle at room temperature with a mechanical shaker. The gel was extensively washed as described above. The unreacted aldehyde groups on the agarose matrix were then reduced with a solution 1 M $NaBH_4$ [1 ml per each milliliter of agarose gel] for 15 hours at 4°. The substituted agarose was washed extensively again. The substitution of ligand was about 2 μmoles per milliliter of agarose when 50 mM diaminodipropylamine was used.

Hydrazidosuccinyl-Agarose

Preparation of Succinic Dihydrazide (SDH)

Sixty-four grams (2 moles) of hydrazine (99%) were stirred magnetically in a 1-liter Erlenmeyer flask with 100 ml of absolute ethanol at room temperature. Diethyl succinate (35 g; 0.2 mole) was added dropwise over 3-4 hours from a dropping funnel. The temperature of the reaction mixture was raised to 45°-50°. The clear reaction mixture was allowed to stand overnight at room temperature, and the resultant crystalline succinic dihydrazide (SDH) was filtered, washed with a liter of ice-cold absolute ethanol, and dried. The dihydrazide (mp 168-170 with decomposition), obtained in 90% yield (26.5 g), was used without further purification.

Use of Periodate-Oxidized Agarose

A suspension containing 100 ml of oxidized agarose and 100 ml of 0.1 M SDH (pH adjusted to 5.0) was gently shaken for 1-2 hours at room temperature and the pH was raised to 9 with solid $Na_2CO_3$. Ten milliliters of freshly prepared aqueous $NaBH_4$ (5 M) was added in small aliquots, with gentle stirring at 4°, over a 12-hour period (avoiding excessive foaming). The reduced agarose derivative was washed on a 250 ml sintered-glass funnel with 2 liters of 1 M NaCl without suction over a 3 to 4-hour period. The agarose derivative was incubated with an equal volume of 1 M NaCl for 15 hours at 24° in the same funnel, by stopping the outflow with a rubber stopper. It was washed with an additional 2 liters of 1 M NaCl over 2-3 hours. The substitution of SDH, calculated from the total nitrogen content of the hydrazidoagarose, varied between 1 and 2 μmoles per milliliter of packed agarose.

Activation and Use of Hydrazido-Agarose

The hydrazido-agarose derivative was stable for months when stored at 4° in the presence of 0.02 M $NaN_3$. Carboxylic group-containing ligands are coupled to the hydrazido-agarose with the use of carbodiimide reagents by established procedures. Cuatrecasas, *J. Biol. Chem.*, supra; Hoare et al, *J. Biol. Chem.*, 242, 2447 (1967). Primary or secondary amines are also coupled readily to the hydrazido-agarose after formation of agarose-azide derivatives with $NaNO_2$ and dilute hydrochloric acid, as described below.

Preparation and Use of Hydrazido-Cellulose

Preparation

Cellulose fibers or beaded, porous cellulose [Pharmacia], 10 g were suspended in 1 liter of 0.5 M sodium metaperiodate. The slurry was shaken at room temperature. After 2 hours, 30 ml (0.54 mole) of ethylene glycol were added and the slurry was shaken for an additional hours. The oxidized beads were washed on a coarse sintered-glass funnel with 10 portions of 200 ml each of water. The washed gel was adjusted to a 1:1 slurry with water. SDH (4 g, 27 mmoles, in 29 ml of water) was added, the slurry was stirred and the pH was adjusted to 5 with concentrated HCl. After 1 hour the pH was adjusted to 9 with solid sodium carbonate. Sodium borohydride (1 g, 27 mmoles) was added, and the slurry was shaken overnight in a vented container. The beads were washed with 200 ml of 0.1 M acetic acid followed by five washes of 400 ml each of water and stored as a 1:1 slurry in water. Table 1 shows the incorporation of SDH.

Activation and Reaction

The derivatized beads were activated by a modification of the method used by Inman and Dintzis, *Biochemistry*, 8, 4074 (1969). One volume of a mixture of concentrated HCl and concentrated $H_3PO_4$ (90:10; v:v) was added to 10 volumes of a chilled 1:1 slurry of SDH beads. One volume of chilled 1 M $NaNO_2$ was added, and the suspension was stirred in an ice bath for 1-2 minutes. One volume of about 12 M sodium hydroxide was added. The concentration of the base was such that equal volumes of the mixed acid and the base, diluted in water, produced a pH near 6. The neutralized suspension was added directly to the coupling solution, which consisted of 10 volumes of 0.2 M sodium bicarbonate at pH 9.5, containing an appropriate concentration of ligand. The slurry was shaken at 4° for 2 hours and then washed extensively with the appropriate buffers. The amount of alanine and albumin coupled to the gels by this method is indicated in Table 1. The use of SDH in this method provides an intrinsic, "active" spacer on the gel. Furthermore, the hydrazido-agarose derivatives are especially useful for immobilizing glycoproteins, oligosaccharides, or glycolipids which can be oxidized by $NaIO_4$.

Stable Activated Derivatives of Agarose

Agarose derivatives containing stable "activated" functional groups are convenient for routine applications. The hydrazido derivatives of agarose are used, by simple and mild procedures, to immobilize proteins and complex group-containing ligands to agarose, without interfering or complicating reactions. For example, it is very difficult to couple amino acids through their amino group to carboyxlic-agarose derivatives without selectively blocking other functional groups of the amino acid. The principal alternative procedures for coupling amino group containing ligands to derivatized agarose involve the use of water-soluble carbodiimide reagents or alkylating groups [Cuatrecasas, *J. Biol. Chem.*, supra; Cuatrecasas et al, *Enzymology*, 22 [31] (1972)] and require much longer reaction periods, are much less specific for amino groups [especially alkylating agarose derivatives], result in complicating side reactions if the ligand contains other functional groups, and are less likely to proceed to completion.

If it is desired to place the protein at a distance from the matrix backbone by coupling to hydrocarbon extensions attached to the polymer, the current alternative procedures that can be used will [a] result in reaction of tyrosyl or histidyl residues of the protein (diazonium derivatives); [b] lead to molecular cross-linking and polymerization reactions of the protein (carbodiimide reagents); and [c] result in slow reactions which do not discriminate between amino, imidazole, phenolic, or sulfhydryl groups of the protein (bromoacetyl derivatives). The subject activated agarose derivatives, on the other hand, react rapidly and almost exclusively with amino groups of the protein under very mild conditions.

Hydrazido Derivatives of Agarose

This type of "activated" agarose has general properties comparable to those of the known N-hydroxysuccinimide ester derivatives. Immediately before use, the acylhydrazide groups of these derivatives are converted to the corresponding azide form by a simple reaction with $NaNO_2$ in dilute acid. The acyl azide agarose reacts rapidly with amino group-containing ligands. By selecting a pH near 6 for the coupling reaction, substitution can be directed to occur relatively specifically with $\alpha$-$NH_2$ groups relative to $\epsilon$-$NH_2$ groups of peptides or proteins.

The hydrazido-agarose derivatives are prepared by reaction of succinic dihydrazide with $NaIO_4$ activated agarose. Hydrazido derivatives of agarose substituted with macromolecular spacer arms are prepared by hydrazinolysis of the ester functions which are formed on reaction of bromoacetic ester with derivatives such as poly-L-lysine-agarose or poly(L-lysyl-DL-alanine)-agarose.

Preparation of Hydrazido Derivatives of Agarose

Hydrazido derivatives of agarose, prepared by the reaction of succinic dihydrazide with sodium periodate-oxidized agarose have been described above. The hydrazido derivatives of agarose gels which contain macromolecular arms offer many special advantages over the succinic dihydrazido-agarose. Depending on the size and molecular weight of the polyfunctional macromolecule used, the ligand or protein to be coupled can be very conveniently separated from the agarose matrix by distances of varying length; approximately 150 A with poly(L-lysyl-DL-alanine) of 37,500 daltons.

Poly-(L-lysyl-DL-alanyl-hydrazido)-Agarose

The agarose derivative of poly-(L-lysyl-DL-alanine), prepared by the $NaIO_4$ method, was converted to a poly-N-carboxymethyl ester by reaction with bromoacetic ester [Eastman]. The polyester was then converted to the hydrazide form by treatment with aqueous hydrazine.

Poly-(L-lysyl-DL-alanine)-agarose, 10 ml, was suspended in 10 ml of saturated sodium borate and 1.5 ml of 2-bromoacetic ester was added. The suspension was gently shaken overnight in a tightly closed polyethylene bottle at 24°. The agarose derivative was washed over a sintered-glass funnel with 100 ml of water and 100 ml of dioxane. The agarose cake was suspended in 10 ml of 5 M aqueous hydrazine solution. The suspension, after shaking gently for an additional 8–10 hours at 24°, was filtered and washed extensively with 1 M NaCl solution until the TNBS test for hydrazine in the wash was negative. The reaction was performed in a well-ventilated hood.

Coupling Ligands to Hydrazido-Agarose

The coupling of amino group-containing ligands and proteins to hydrazido-agarose was performed by essentially the same method as described in Inman et al, *Biochemistry*, supra. Because of the very limited stability of the intermediate acyl azido formed by nitrous acid, the time and temperature of the activation and coupling reactions was carefully controlled.

Poly-(L-lysyl-DL-alanyl-hydrazido)-agarose, 10 ml, was suspended in 8 ml of water, and 2 ml of 1 M HCl were added. The suspension was cooled in an ice bath for 30 minutes and, while stirring, 2 ml of an ice-cold solution of 1 M $NaNO_2$ was added dropwise over 1 minute periods. The suspension was stirred for an additional 2–3 minutes, then rapidly (1–2 minutes) filtered with suction on a coarse sintered-glass funnel (previously cooled) and washed with 20–30 ml of cold 5 mM HCl. The outlet of the sintered-glass funnel was covered with Parafilm, and a 50 mM solution of [$^{14}$C]-L-alanine (0.1 $\mu$Ci/$\mu$mole) in a 0.2 M sodium bicarbonate at pH 8, was added while being stirred with a glass rod. The suspension was transferred to a polyethylene vial and shaken gently for 15 hours at 4°. The substituted agarose was washed extensively with 1 M NaCl. Substitution of [$^{14}$C]alanine was about 1 $\mu$mole per milliliter of agarose.

Preparation of Hydrazido-Albumin

Another approach to the preparation of hydrazido macromolecular derivatives is to synthesize hydrazido-albumin, which can then be coupled to agarose, stored in buffer, and activated for use when needed. Hydrazido-albumin is prepared by esterifying the aspartate and glutamate carboxyl groups with methanol, HCl being used as the catalyst. The esterified albumin is then treated with hydrazine to convert the esters to acyl hydrazides. The hydrazido-albumin is coupled to agarose in denaturing solvents (urea or guanidine HCl) with CNBr. These agarose beads are then activated by reaction with dilute nitrous acid to convert the hydrazido groups to acyl azide groups. The latter can react rapidly with amines to form amides.

Hydrazido-albumin is prepared by dissolving 5 g of bovine albumin in 100 ml of anhydrous methanol and adding 72 mg (20 mmoles) of anhydrous HCl gas. The solution is stirred overnight at room temperature. A white precipitate forms which is collected by filtration, washed once with ethanol, and suspended in 100 ml of anhydrous ethanol. Hydrazine (3.2 g, 300 mmoles) is added and allowed to react for 20 hours at room temperature while the suspension is stirred. The solvents are removed on a vacuum evaporator, and the residue is suspended in ethanol and dried again. The residue is dissolved in 6 M quanidine HCl to give a final concentration of 10 mg/ml. One volume of the protein solution is added to 1 volume of 0.2 M NaHCO$_3$ at pH 9.5, and allowed to react with 2 volumes of CNBr-activated agarose by the buffer activation method. The hydrazido-albumin-agarose is activated with nitrous acid as described above. Preliminary studies with insulin as a test ligand indicate that the coupling efficiency of this macromoleclar gel is about 10% of that of CNBr-activated agarose.

While the invention has been shown and described and pointed out with reference to certain preferred embodiments thereof, those skilled in the art will appreciate that various changes, modifications, substitutions, and omissions can be made by those skilled in the art without departing from the spirit of the invention. It is intended, therefore, that the invention be limited only by the scope of the claims which follow.

What is claimed is:

1. In the method for the activation of a polysaccharide matrix for use as an adsorbent in affinity chromatography techniques, comprising activating the said polysaccharide by oxidizing the cis-vicinal hydroxyl groups thereof with sodium metaperiodate to generate aldehyde functions, converting said aldehydic functions into Schiff bases and thence reductively stabilizing the said resultant Schiff bases, the improvement which comprises the reductive stabilization of said intermediate Schiff bases with sodium cyanoborohydride at a pH between 6 and 6.5.

2. In the method as defined by claim 1, the improvement further comprising the preferential, selective reductive stabilization of the said intermediate Schiff bases in the absence of a reduction of the aldehyde functions of the polysaccharide.

3. In the method as defined by claim 2 wherein the polysaccharide is agarose.

4. The method for the preparation of a hydrazide-polysaccharide derivative for use as an adsorbent in affinity chromatography techniques, which comprises activating a polysaccharide matrix by oxidizing the cis-vicinal hydroxyl groups thereof with sodium metaperiodate to generate aldehyde functions, reacting said periodate-oxidized polysaccharide with a bifunctional, symmetrical dihydrizide to convert the same to the corresponding hydrazido/hydrazone derivative, and thence reductively stabilizing said hydrazido/hydrazone derivative with sodium cyanoborohydride at a pH between 6 and 6.5 to produce an unsemetric hydrazide.

5. The method as defined by claim 4, wherein the bifunctional, symmetrical dihydrazide is succinic dihydrazide.

6. The method as defined by claim 5, wherein the resultant unsymmetric hydrazide bears unreacted hydrazido moieties.

7. In a method for the affinity chromatographic technique of coupling proteins or ligands, bearing carbonyl or amino moieties, to a polysaccharide matrix, the improvement which comprises derivatizing the matrix as defined in claim 6, coupling a said protein or ligand to the polyhydrazide-matrix and thence reductively stabilizing said protein- or ligand-hydrazido-polysaccharide.

8. The method as defined by claim 7, wherein the reductive stabilization of the coupled complex is effected with sodium cyanoborohydride.

9. The method as defined by claim 7, wherein a spacer molecule is interposed between the derivatized matrix and the protein or ligand coupled thereto.

10. The method as defined by claim 7, wherein the polysaccharide is selected from the group consisting of cellulose, starch, cross-linked dextran and agarose.

11. The method as defined by claim 10, wherein the polysaccharide is agarose.

12. The method as defined by claim 7, wherein the molecule coupled to the polysaccharide matrix is selected from the group consisting of glycolipid, ganglioside, glycoprotein, glycopeptide, oligosaccharide, brain ganglioside and thyroglobin.

13. The product of the method as defined by claim 1.

14. The product of the method as defined by claim 4.

15. The product of the method as defined by claim 7.

16. The product of the method as defined by claim 9.

17. The method as defined by claim 7, wherein the protein or ligand to be coupled is preliminarily oxidized with sodium metaperiodate.

18. In an affinity chromatography column comprising an insoluble, solid polysaccharide adsorbent, the improvement which comprises, as the said adsorbent or matrix thereof, the product as defined by claim 14.

19. In the method as defined by claim 2, the improvement where in the polysaccharide is selected from the group consisting of cellulose, starch, cross-linked dextran and agarose.

* * * * *